(12) United States Patent
Hoffa

(10) Patent No.: US 7,753,868 B2
(45) Date of Patent: Jul. 13, 2010

(54) MULTI-LUMEN CATHETER

(75) Inventor: Andrew K. Hoffa, Bloomington, IN (US)

(73) Assignee: Cook Critical Care Incorporated, Bloomington, IN (US)

( * ) Notice: Subject to any disclaimer, the term of this patent is extended or adjusted under 35 U.S.C. 154(b) by 249 days.

(21) Appl. No.: 11/842,341

(22) Filed: Aug. 21, 2007

(65) Prior Publication Data

US 2009/0054826 A1    Feb. 26, 2009

(51) Int. Cl.
*A61M 35/00*    (2006.01)
*A61M 3/00*    (2006.01)
*A61M 25/00*    (2006.01)

(52) U.S. Cl. .................. 604/4.01; 604/43; 604/264

(58) Field of Classification Search ....... 604/4.01–6.16, 604/43, 264–266, 270, 523–528, 541
See application file for complete search history.

(56) References Cited

U.S. PATENT DOCUMENTS

| | | | |
|---|---|---|---|
| 3,938,530 A | 2/1976 | Santomieri | 128/349 R |
| 3,946,741 A | 3/1976 | Adair | 128/347 |
| 4,129,129 A | 12/1978 | Amrine | 128/214 R |
| 4,134,402 A | 1/1979 | Mahurkar | 128/214 R |
| 4,154,242 A | 5/1979 | Termanini | 128/349 R |
| 4,493,696 A | 1/1985 | Uldall | 604/43 |
| RE31,855 E | 3/1985 | Osborne | 604/161 |
| 4,568,329 A | 2/1986 | Mahurkar | 604/43 |
| 4,581,025 A | 4/1986 | Timmermans | 604/264 |
| 4,583,968 A | 4/1986 | Mahurkar | 604/43 |
| 4,643,711 A | 2/1987 | Bates | 604/4 |
| 4,655,745 A | 4/1987 | Corbett | 604/49 |
| 4,680,029 A | 7/1987 | Ranford et al. | 604/280 |
| 4,692,141 A | 9/1987 | Mahurkar | 604/43 |
| 4,733,669 A | 3/1988 | Segal | 128/663 |
| 4,769,005 A | 9/1988 | Ginsburg et al. | 604/53 |
| 4,772,268 A | 9/1988 | Bates | 604/174 |
| 4,808,163 A | 2/1989 | Laub | 604/105 |
| 4,878,893 A | 11/1989 | Chin | 604/21 |
| 4,904,238 A | 2/1990 | Williams | 604/43 |
| 4,936,826 A | 6/1990 | Amarasinghe | 604/52 |

(Continued)

FOREIGN PATENT DOCUMENTS

EP    0 301 854 A2    2/1989

(Continued)

*Primary Examiner*—Leslie R Deak
*Assistant Examiner*—Philip R Wiest
(74) *Attorney, Agent, or Firm*—Brinks Hofer Gilson & Lione

(57) ABSTRACT

A catheter for use in extracorporeal treatment of a bodily fluid includes an elongated tubular member having a pair of lumens extending therein, and a septum separating the lumens. A first lumen comprises a withdrawal lumen, and a second lumen comprises an infusion lumen. A withdrawal port disposed along a length of the tubular member communicates with the withdrawal lumen for receiving fluid from a body vessel for transport to a treatment unit, such as a dialyzer. An infusion port disposed along a length of the tubular member communicates with the infusion lumen for returning treated fluid to the vessel. A passageway is formed in an outer wall of the tubular member adjacent the infusion lumen and extends through the septum. A generally tubular conduit extends through the passageway such that the withdrawal lumen communicates with an environment exterior of the tubular member outer wall.

18 Claims, 3 Drawing Sheets

U.S. PATENT DOCUMENTS

| | | | |
|---|---|---|---|
| 4,973,301 A | 11/1990 | Nissenkorn | 604/8 |
| 4,995,865 A | 2/1991 | Gahara et al. | 604/43 |
| 4,995,868 A | 2/1991 | Brazier | 604/105 |
| 5,106,368 A | 4/1992 | Uldall et al. | 604/43 |
| 5,156,597 A | 10/1992 | Verreet et al. | 604/175 |
| 5,193,533 A | 3/1993 | Body et al. | 128/207.14 |
| 5,221,256 A | 6/1993 | Mahurkar | 604/43 |
| 5,250,034 A | 10/1993 | Appling et al. | 604/164 |
| 5,275,610 A | 1/1994 | Eberbach | 606/198 |
| 5,352,198 A | 10/1994 | Goldenberg et al. | 604/95 |
| 5,360,397 A | 11/1994 | Pinchuk | 604/27 |
| 5,364,344 A | 11/1994 | Beattie et al. | 604/43 |
| 5,403,291 A | 4/1995 | Abrahamson | 604/280 |
| 5,409,460 A | 4/1995 | Krumme | 604/107 |
| 5,443,449 A | 8/1995 | Buelna | 604/105 |
| 5,486,159 A * | 1/1996 | Mahurkar | 604/6.16 |
| 5,489,278 A | 2/1996 | Abrahamson | 604/280 |
| 5,509,897 A | 4/1996 | Twardowski et al. | 604/43 |
| 5,509,900 A | 4/1996 | Kirkman | 604/104 |
| 5,514,112 A | 5/1996 | Chu et al. | 604/267 |
| 5,518,498 A | 5/1996 | Lindenberg et al. | 600/30 |
| 5,522,400 A | 6/1996 | Williams | 128/772 |
| 5,571,093 A | 11/1996 | Cruz et al. | 604/270 |
| 5,681,280 A | 10/1997 | Rusk et al. | 604/95 |
| 5,702,365 A | 12/1997 | King | 604/105 |
| 5,713,853 A | 2/1998 | Clark et al. | 604/53 |
| 5,749,826 A | 5/1998 | Faulkner | 600/29 |
| 5,817,067 A | 10/1998 | Tsukada | 604/256 |
| 5,857,464 A | 1/1999 | Desai | 128/658 |
| 5,885,258 A | 3/1999 | Sachdeva et al. | 604/281 |
| 5,888,196 A | 3/1999 | Bonutti | 600/204 |
| 5,957,900 A | 9/1999 | Ouchi | 604/264 |
| 6,001,079 A | 12/1999 | Pourchez | 604/43 |
| 6,033,397 A | 3/2000 | Laufer et al. | 606/27 |
| 6,052,612 A | 4/2000 | Desai | 600/435 |
| 6,071,263 A | 6/2000 | Kirkman | 604/104 |
| 6,177,049 B1 | 1/2001 | Schnell et al. | 422/44 |
| 6,238,412 B1 | 5/2001 | Dubrul et al. | 606/200 |
| 6,270,490 B1 | 8/2001 | Hahnen | 604/509 |
| 6,283,940 B1 | 9/2001 | Mulholland | 604/96.01 |
| 6,293,958 B1 | 9/2001 | Berry et al. | 606/191 |
| 6,336,933 B1 | 1/2002 | Parodi | 606/139 |
| 6,409,700 B1 | 6/2002 | Siegel, Jr. et al. | 604/43 |
| 6,454,775 B1 | 9/2002 | Demarais et al. | 606/128 |
| 6,461,321 B1 | 10/2002 | Quinn | 604/43 |
| 6,475,207 B1 | 11/2002 | Maginot et al. | 604/508 |
| 6,482,169 B1 | 11/2002 | Kuhle | 604/6.16 |
| 6,517,529 B1 | 2/2003 | Quinn | 604/528 |
| 6,527,737 B2 | 3/2003 | Kaneshige | 604/48 |
| 6,547,761 B2 | 4/2003 | Liu | 604/104 |
| 6,558,349 B1 | 5/2003 | Kirkman | 604/104 |
| 6,558,350 B1 | 5/2003 | Hart et al. | 604/104 |
| 6,569,150 B2 | 5/2003 | Teague et al. | 604/524 |
| 6,579,302 B2 | 6/2003 | Duerig et al. | 606/198 |
| 6,758,836 B2 | 7/2004 | Zawacki | 604/284 |
| 6,767,339 B2 | 7/2004 | Reydel | 604/175 |
| 6,966,886 B2 | 11/2005 | Appling | 604/6.16 |
| 2001/0011182 A1 | 8/2001 | Dubrul et al. | 606/200 |
| 2001/0018576 A1 | 8/2001 | Quinn | 604/264 |
| 2002/0072768 A1 | 6/2002 | Ginn | 606/213 |
| 2002/0143292 A1 | 10/2002 | Flinchbaugh | 604/107 |
| 2002/0177822 A1 | 11/2002 | St. Cyr et al. | 604/264 |
| 2003/0032918 A1 | 2/2003 | Quinn | 604/43 |
| 2003/0139763 A1 | 7/2003 | Duerig et al. | 606/198 |
| 2005/0148929 A1 | 7/2005 | Gingles | 604/95.04 |
| 2005/0261663 A1 | 11/2005 | Patterson et al. | 604/508 |
| 2006/0253063 A1 | 11/2006 | Schweikert | 604/30 |
| 2007/0016124 A1* | 1/2007 | McGraw | 604/4.01 |

FOREIGN PATENT DOCUMENTS

| | | |
|---|---|---|
| WO | WO 01/19425 A1 | 3/2001 |
| WO | WO 02/064202 A3 | 8/2002 |
| WO | WO 2005/049125 A1 | 6/2005 |

* cited by examiner

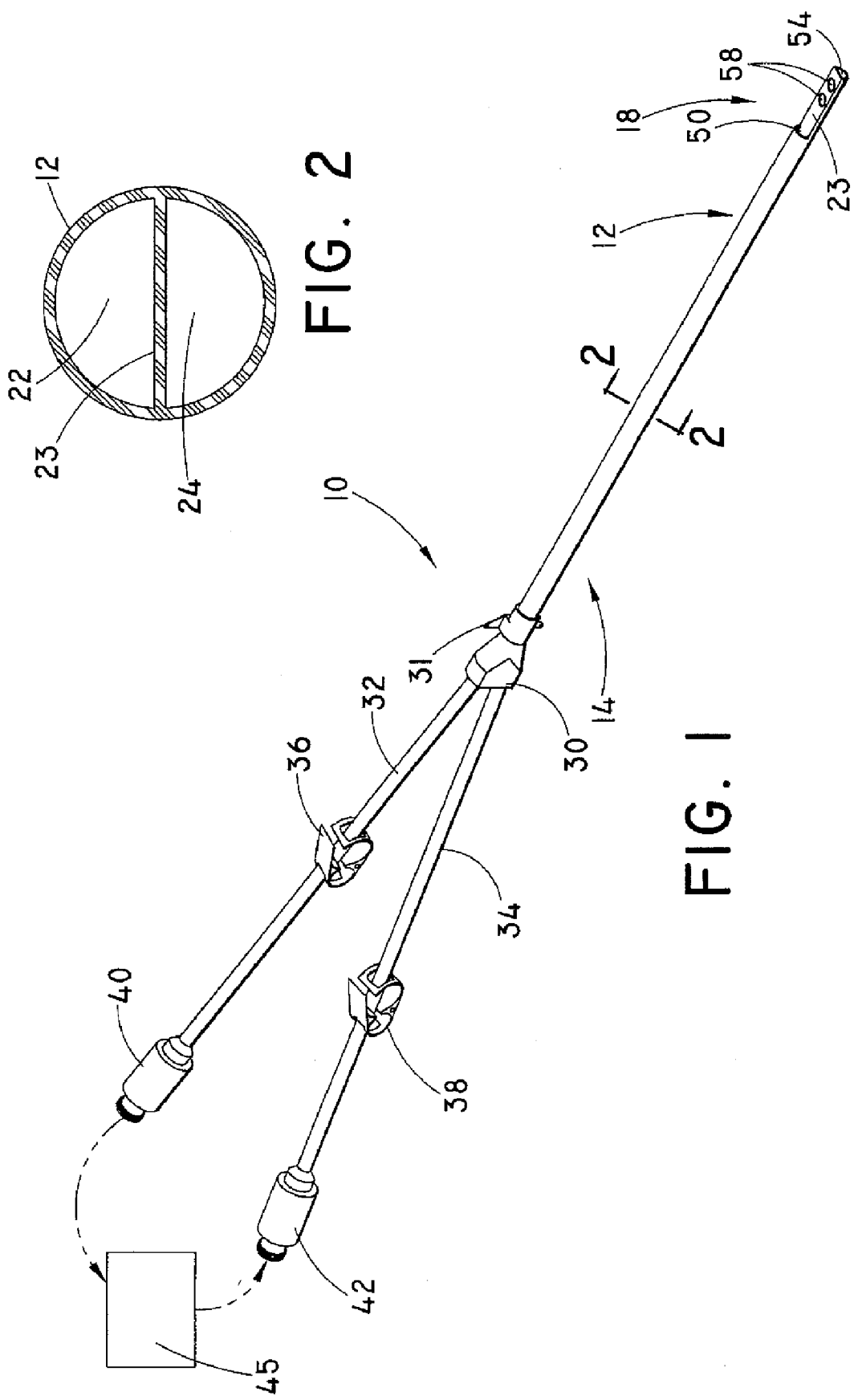

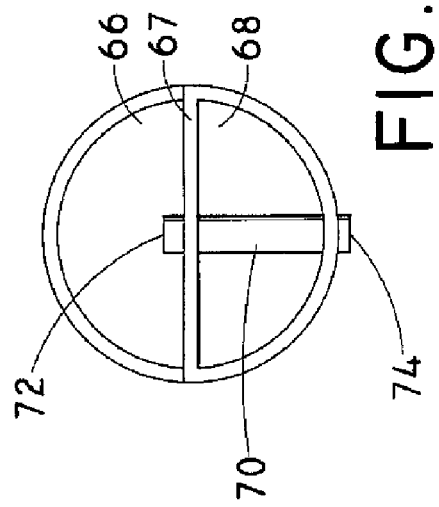
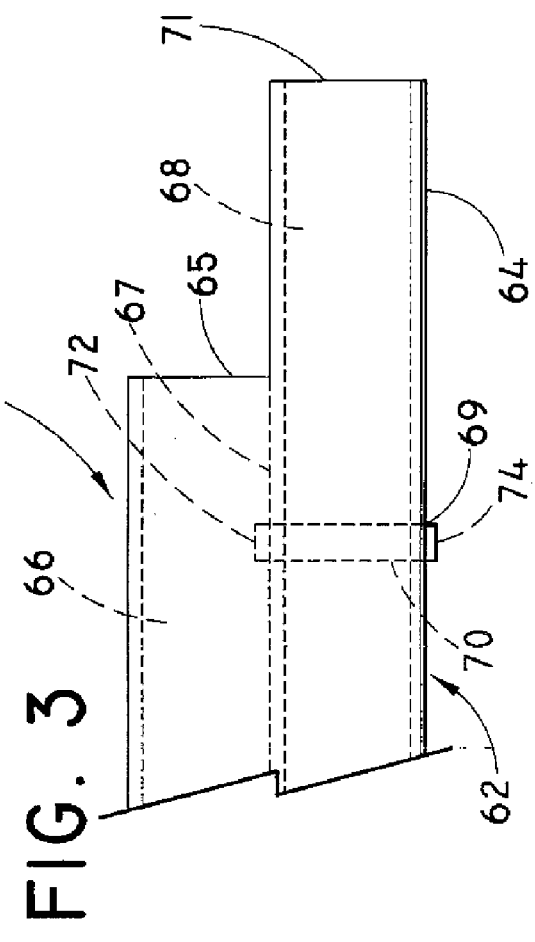
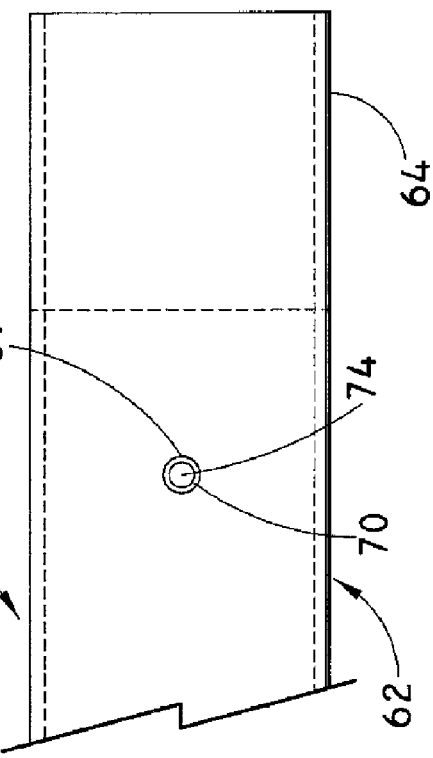

MULTI-LUMEN CATHETER

BACKGROUND

1. Technical Field

This application relates generally to a catheter for use in transporting fluids, and more particularly, to a multi-lumen catheter for transporting bodily fluids for extracorporeal treatment, and returning the treated fluids to the body.

2. Background Information

Multi-lumen catheters are commonly used for transport of a bodily fluid during an extracorporeal treatment process for the bodily fluid. A fluid is withdrawn from the body through one of the lumens, generally referred to as the withdrawal lumen. The fluid is subjected to a treatment process, and thereafter returned to the body through another lumen, generally referred to as the infusion lumen.

In many cases, the extracorporeal treatment involves a hemodialysis procedure. During hemodialysis, blood is withdrawn from a blood vessel through the withdrawal lumen (also commonly referred to as the arterial lumen), and routed to a dialyzer for treatment. The cleansed blood is then returned to the vessel through the infusion lumen (also commonly referred to as the venous lumen). When such a catheter is used for hemodialysis, it is generally inserted into the body through the jugular vein, subclavian vein or femoral vein. In addition to hemodialysis, extracorporeal catheters can also be used for other procedures, such as pheresis and hemofiltration, in which a fluid is removed from the body for treatment and later returned to the body.

A variety of hemodialysis catheters are commercially available. Among the types of commercially available catheters are: 1) a dual lumen catheter having staggered lumens, wherein one lumen (e.g., the blood infusion lumen) terminates distal to the other lumen (e.g., the blood withdrawal lumen). Some catheters of this type are provided with a midline split (e.g., the Uldall catheter), while others do not have such a split (e.g., the COOK® DDS catheter); 2) catheters having a slitted valve in the distal tip that acts as a pressure valve opening. This valve opens inwardly for blood aspiration, outwardly for blood infusion, and remains closed when not in use (e.g., the Groshong catheter); 3) cuffed central venous silicone catheters that are tunneled underneath the skin to reduce infection (e.g., Broviac, Leonard and Hickman catheters); 4) dual lumen catheters having a tapered tip and two adjacent holes communicating with one lumen just proximal to the tip to assist with outflow, and two adjacent holes communicating with the other lumen (180 degrees removed) just proximal to the first set of holes to assist with inflow (e.g., the Mahurkar catheter); 5) dual lumen catheters having a diverting structure consisting of a shoulder that has a straight up distal face and a sloped proximal face to reduce access recirculation and raise pressure in the vicinity of the inlet aperture (U.S. Pat. No 6,409,700); and 6) catheters designed for femoral approach having two sets of staggered side ports, resulting in a total of four side ports.

One problem with existing extracorporeal catheters is that such catheters can experience decreased flow rates over time. Decreased flow rates may be caused by, among other things, blockage of the withdrawal and/or infusion ports in the catheter. Various factors can cause a port to become blocked. One common cause of port blockage is the inadvertent positioning of one or more ports of the catheter against the vessel wall. This positioning hinders the free flow of fluid through the obstructed port, and in some cases, prevents fluid flow altogether. Another common cause of port blockage is the formation of fibrin sheaths along the ports. Fibrin sheaths may be formed, e.g., in response to the vessel wall washing effect or clotting.

Decreased, or restricted, flow is clearly undesirable in an extracorporeal catheter, such as a hemodialysis catheter. In order for the extracorporeal fluid treatment process to be effective, fluid flow through the catheter must not be restricted in any appreciable way. Thus, it is important to position the catheter in a manner such that fluid flow is not restricted. Additionally, it is important to insure that the ports are unobstructed.

Various attempts have been made in the art to reduce port blockage. For example, as described above, some catheters are provided with side ports at various locations on the catheter. Side ports generally provide some reduction in port blockage, however such ports themselves are subject to blockage when placed against the vessel wall, or as a result of fibrin formation on the port. Other attempts have been made to reduce port blockage by providing the staggered side-by-side dual lumen design described above, wherein the respective withdrawal and infusion tubes are of different lengths so that the ports withdraw and infuse the bodily fluid at different axial locations of the catheter. While this arrangement may avoid some problems involved in maintaining adequate flow through the lumens, such catheters can still be subject to suboptimal flow. Some catheters, such as the Mahurkar catheter described above, must be rotated if inflow is blocked because the catheter is up against the vein wall. Although each of these techniques may be at least partially effective in reducing some types of blockage, reduced flow rate continues to be a problem in the art.

It is desired to provide a multi-lumen catheter for use in the extracorporeal treatment of bodily fluids, wherein the multi-lumen catheter is structured in a manner to minimize port blockage, and to provide for optimal fluid flow through the lumens of the catheter.

SUMMARY

The present invention addresses the shortcomings of the prior art. In one form thereof, the invention comprises a multi-lumen catheter comprising an elongated tubular member having a plurality of lumens extending therein. The tubular member has a withdrawal port in communication with a first lumen for transporting fluid withdrawn from a body vessel, and an infusion port in communication with a second lumen for return of fluid to the body vessel. The withdrawal port is positioned proximal of the infusion port along a length of the tubular member. The tubular member includes a septum separating the first and second lumens, and extending at least substantially to the infusion port. The tubular members are configured such that at least a portion of the septum extending between the withdrawal port and the infusion port is uncovered. The uncovered portion of the septum includes at least one aperture.

In another form thereof, the present invention comprises a multi-lumen catheter comprising an elongated tubular member having a plurality of lumens extending therein. The tubular member has a withdrawal port in communication with a first lumen for transporting fluid withdrawn from a body vessel, and an infusion port in communication with a second lumen for return of treated fluid to the vessel. The withdrawal port is positioned proximal of the infusion port along a length of the tubular member. The tubular member includes a septum separating the first and second lumens. The tubular member further comprises a passageway formed in an outer wall of the tubular member adjacent the infusion lumen and extending through the septum to the withdrawal lumen, and a generally tubular conduit extending through the passageway, such that the withdrawal lumen communicates with an environment exterior of the tubular member outer wall.

In still another form thereof, the present invention comprises a multi-lumen catheter for use in extracorporeal treatment of a bodily fluid of a patient. The catheter comprises an elongated tubular member having a pair of lumens extending therein. A septum separates the lumens in an interior space of the elongated member. A first lumen comprises the withdrawal lumen, and a second lumen comprises the infusion lumen. A withdrawal port is disposed along a length of the tubular member in communication with the withdrawal lumen for receiving the bodily fluid from a body vessel for transport to a treatment unit, and an infusion port disposed along a length of the tubular member in communication with the infusion lumen for returning treated body fluid to the vessel. The tubular member further comprises a passageway formed in an outer wall of the tubular member adjacent the infusion lumen and extending through the septum, and a generally tubular conduit extending through the passageway such that the withdrawal lumen communicates with an environment exterior of the tubular member outer wall.

BRIEF DESCRIPTION OF THE DRAWINGS

FIG. 1 is a perspective view of a multi-lumen catheter according to an embodiment of the present invention;

FIG. 2 is an enlarged sectional view of the catheter of FIG. 1, taken along line 2-2;

FIG. 3 is an enlarged side view of the distal portion of another embodiment of a multi-lumen catheter;

FIG. 4 is an end view of the catheter of FIG. 3;

FIG. 5 is a side view of the catheter of FIG. 3, rotated 90 degrees from the orientation as shown in FIG. 3;

DETAILED DESCRIPTION OF THE DRAWINGS AND THE PRESENTLY PREFERRED EMBODIMENTS

Figure 6:
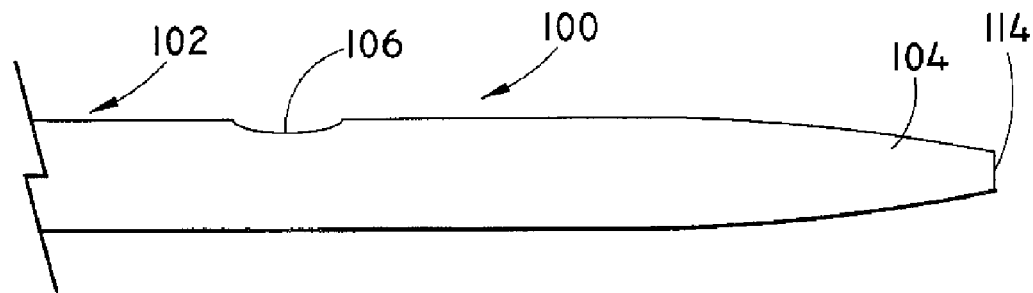
FIG. 6 is a side view of the distal portion of another embodiment of a multi-lumen catheter.

For purposes of promoting an understanding of the present invention, reference will now be made to the embodiments illustrated in the drawings, and specific language will be used to describe the same. The figures are not all drawn to the same scale to avoid obscuring the details of the finer structures. The following detailed description of the preferred embodiments will make clear the preferred arrangement, size relationships and manner of using the components shown herein.

The present invention is directed to a multi-lumen catheter for use in the transport of bodily fluids for treatment external of the body, referred to in the medical arts as "extracorporeal" treatment. The bodily fluids are transported from the body through a withdrawal lumen in the catheter, and are thereafter transported to an instrument for extracorporeal treatment. The treated fluids are then returned to the body through an infusion lumen in the catheter.

Those skilled in the art will appreciate that the catheter described herein is suitable for multiple uses involving inflow and outflow of bodily fluids. For convenience, the invention will be primarily described hereinafter with reference to one of its intended uses, namely as a hemodialysis catheter for use in the extracorporeal treatment of blood. The hemodialysis catheter enables blood inflow without disturbance, and blood return without hemolysis. In addition to hemodialysis, the catheter can be used for other extracorporeal fluid treatments in which a body fluid is withdrawn from the body, subjected to a treatment process, and thereafter returned to the body. Pheresis and hemofiltration are non-limiting examples of such additional procedures.

In the following discussion, the terms "proximal" and "distal" will be used to describe the axial ends of the catheter, as well as the axial ends of various component features. The "proximal" end is used in conventional manner to refer to the end of the catheter (or component) that is closest to the operator during use of the assembly. The "distal" end is used in conventional manner to refer to the end of the catheter (or component) that is initially inserted into the patient, or that is closest to the patient.

FIG. 1 illustrates a perspective view of a multi-lumen catheter 10, according to an embodiment of the present invention. Catheter 10 may be used for transporting bodily fluids for use in an extracorporeal treatment, such as hemodialysis, and returning the treated fluids to the body. Catheter 10 includes an elongated flexible tubular member 12 having a proximal end 14 and a distal end 18, and dual lumens 22, 24 extending therethrough (FIG. 2). In the embodiment shown, lumens 22, 24 have a generally D-shaped profile, and are separated by a septum 23. Those skilled in the art will appreciate that the D-shaped profile of the lumens is merely one example, and that other profiles, such as round, may be substituted.

Catheter 10 typically includes a conventional bifurcated fitting at its proximal end, such as hub 30. Hub 30 may be provided with conventional suture wings 31 if desired for engaging the catheter with the skin of the patient. Flexible extension tubes 32, 34 extend in the proximal direction from hub 30. Each extension tube is in fluid communication with a separate one of lumens 22, 24. In the embodiment shown, extension tube 32 is in fluid communication with lumen 22, and extension tube 34 is in fluid communication with lumen 24. Clamps 36, 38 are provided for selectively closing off fluid flow through the respective extension tubes 32, 34. Luer lock or other suitable connecting mechanisms 40, 42 are provided for engagement with a treatment instrument 45, such as a dialyzer, for establishing a flow path of blood to and from the dialyzer. Dialyzer 45 and its ingress and egress openings are shown schematically in FIG. 1.

In the multi-lumen catheter 10 shown in FIG. 1, elongated tubular member 12 includes a stepped axial surface along the length of tubular member distal end portion 18. Stepped axial surfaces in hemodialysis catheters are conventional, and may be formed, e.g., by cutting away a distal portion of tubular member 12 that defines lumen 22, thereby exposing a portion of the septum that would otherwise be covered by the tubular member cut portion. In one preferred embodiment, a discrete distance, such as about 3 cm, is cut from the distal tip of tubular member 12. Those skilled in the art will appreciate that the amount of tubular member 12 cut away can be larger, or smaller, than the exemplary distance described herein.

As illustrated in FIG. 1, catheter 10 is provided with one or more apertures 58 extending through the exposed, or uncovered, portion of septum 23. Apertures 58 establish communication between lumen 24 and the environment external of the catheter. Preferably, at least two apertures 58 will be spaced along the distalmost portion of septum 23, although additional apertures can be provided along the exposed length of septum 23 if desired.

For use in hemodialysis, catheter 10 may be inserted into the blood vessel over a wire guide, e.g., via the well-known Seldinger percutaneous entry technique. Blood is withdrawn, or aspirated, from the vessel through withdrawal port 50, and passes through (arterial) lumen 22 to the dialyzer 45. Treated blood from the dialyzer returns to the vessel through (venous) lumen 24 and infusion port 54. One or more side ports (not shown) may additionally be provided for return of treated fluid to the lumen. Preferably, withdrawal port 50 is positioned proximal to infusion port 54 and any side ports along the length of catheter body 12. Positioning the withdrawal port proximal to the infusion port and side ports assures that the majority of the blood that is aspirated through the withdrawal port for transport to the dialyzer is not the same blood that has previously been cleansed and returned to the vessel through the infusion port and/or side port.

In the present embodiment, apertures 58 provide additional ports for infusion of the treated fluid. By providing apertures 58 through the septum 23 as shown and described, a stream of treated blood passes laterally through each of the apertures. When blood is withdrawn (aspirated) from the vessel through withdrawal port 50, aspiration of the blood has a tendency to draw or suck port 50 against the vessel wall, thereby hindering or even preventing further blood flow through the port. By allowing streams of blood to be laterally-directed against the wall of the blood vessel through apertures 58, withdrawal port 50 is forced away from the vessel wall, thereby preventing blockage of the withdrawal port by the wall.

FIGS. 3-5 illustrate another embodiment of a multi-lumen catheter 60 according to the present invention. FIG. 3 is an enlarged side view of the distal portion of multi-lumen catheter 60, and FIG. 4 is an end view of the catheter of FIG. 3. FIG. 5 is a side view of the catheter of FIG. 3, rotated 90 degrees from the orientation shown in FIG. 3. The proximal portion of catheter 60 is conventional, and may, for example, have the configuration of the catheter proximal portion illustrated in FIG. 1. Further description and illustration of the proximal portion of the catheter is not necessary for an understanding of the inventive aspects of this embodiment.

As with the embodiment of FIG. 1, multi-lumen catheter 60 may comprise an elongated tubular member 62 having a stepped axial surface along the length of tubular member distal end portion 64. Catheter 60 preferably includes D-shaped lumens 66, 68, which lumens are separated by a septum 67. Once again, those skilled in the art will appreciate that the D-shaped profile of the lumens is merely one example, and that other profiles may be substituted.

In the embodiment shown, a very small diameter tubular conduit, such as cannula 70, has open ends 72, 74 and is punched or otherwise inserted through an aperture 69 (FIG. 5) in the side wall of catheter distal end 64. Cannula 70 is sized and positioned such that it extends through the diameter of lumen 68 and passes through septum 67, wherein open cannula end 72 extends or opens into lumen 66. This is best shown in FIG. 4. Typically, cannula 70 will have a diameter of about 0.025 to 0.035 inch (0.635 to 0.889 mm), and a length of about 0.04 to 0.05 inch (1.016 to 1.27 mm). Those skilled in the art will appreciate that these dimensions are provided as examples only, and can be varied in a particular case. Cannula 70 may be formed of any biocompatible composition commonly utilized in the medical arts, such as a plastic, metal, or metal alloy.

With this embodiment, blood may be withdrawn from the vessel into withdrawal lumen 66 in two ways. First, blood is withdrawn through withdrawal port 65 into lumen 66 in conventional fashion. Additionally, however, blood may also be withdrawn from the vessel into lumen 66 through cannula 70. Since cannula open end 74 is on the opposite side of tubular member 62 from withdrawal port 65, cannula 70 provides a mechanism for aspirating blood into withdrawal lumen 66 even in the event that withdrawal port 65 becomes partially or fully occluded Treated blood is then returned to the vessel via infusion lumen 69 and ultimately, through infusion port 71 as well as any side ports (if present), in well-known fashion. If desired, cannula 70 may also be provided with apertures along the uncovered distal portion of septum 77, in the same manner as apertures 58 shown in FIG. 1.

FIGS. 6-9 illustrate another embodiment of a multi-lumen catheter 100 according to the present invention. FIG. 6 is a side view of the distal portion of multi-lumen catheter 100. Once again, the proximal portion of catheter 100 is conventional, and may, for example, have the configuration of the catheter proximal portion illustrated in FIG. 1. Further description and illustration of the proximal portion of the catheter is not necessary for an understanding of the inventive aspects of this embodiment.

Figure 7:
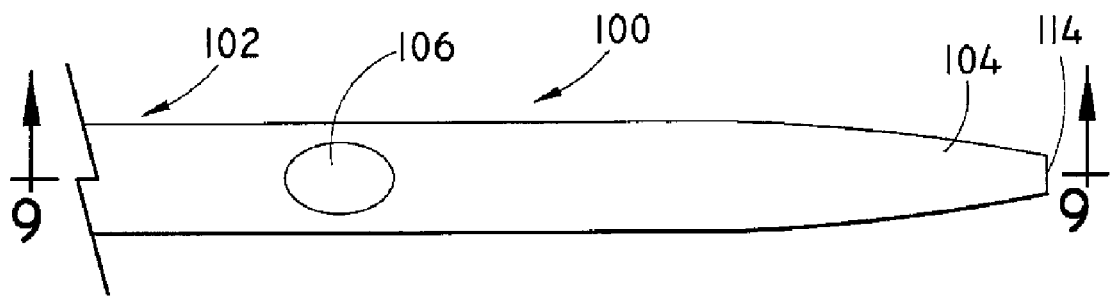
FIG. 7 is a side view of the catheter of FIG. 6, rotated 90 degrees in a first direction from the orientation as shown in FIG. 6.
Figure 8:
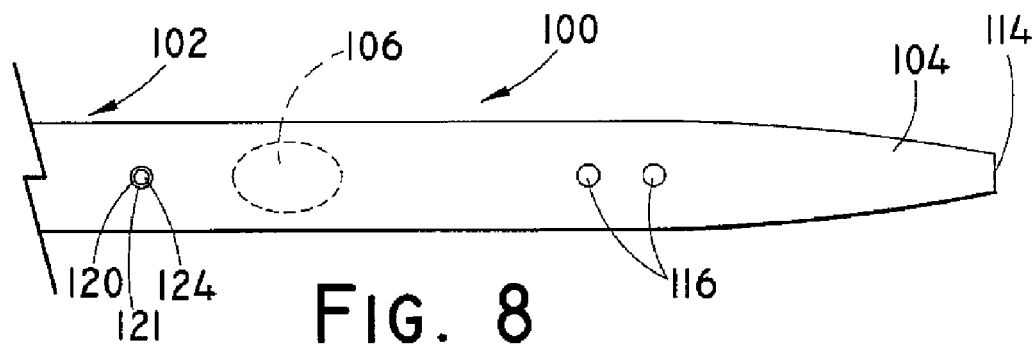
FIG. 8 is another side view of the catheter of FIG. 6, rotated 90 degrees in a second direction, opposite from the first direction, from the orientation as shown in FIG. 6.
Figure 9:
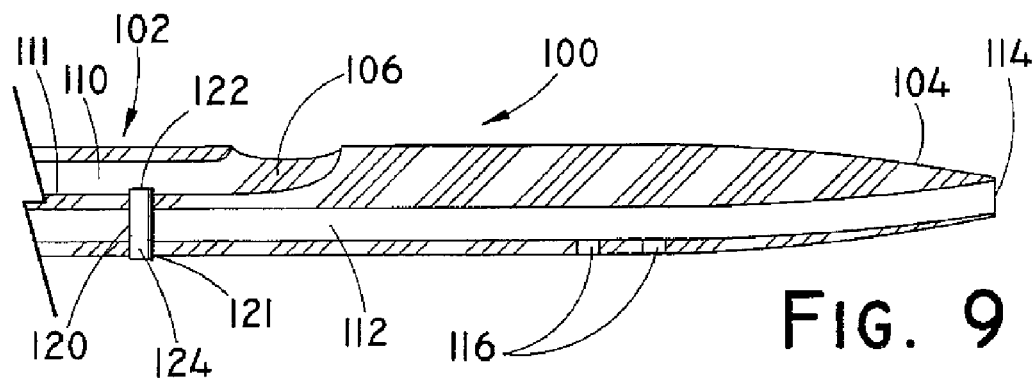
FIG. 9 is a longitudinal sectional view of multi-lumen catheter 100 of FIG. 7.

In the embodiment shown, multi-lumen catheter 100 includes an elongated tubular member 102 that includes a tapered distal end portion 104. Elongated tubular member 102 includes a cut-out portion 106 along its length. FIG. 7 is a side view of the catheter of FIG. 6, rotated 90 degrees in a first direction from the orientation as shown in FIG. 6 to better illustrate the cut-out portion. FIG. 8 is a side view of the catheter of FIG. 6, rotated 90 degrees in a second direction, opposite from the first direction, from the orientation as shown in FIG. 6. FIG. 9 is a longitudinal sectional view of multi-lumen catheter 100.

Multi-lumen catheter 100 includes a withdrawal lumen 110, and an infusion lumen,1 12 (FIG. 9). Lumens 1 10, 112 are separated along at least part of the length of elongated tubular member 102 by septum 111. In this embodiment, cut-out portion 106 comprises the withdrawal port for receiving blood from the vessel for transport to the dialyzer (not shown). Those skilled in the art will appreciate that cut-out portions of other sizes and shapes may be substituted for portion 106 shown in the figures.

An infusion port 114 is provided for infusing treated fluid back into the vessel. In the preferred embodiment shown, infusion port 114 comprises an open distal tip of the catheter. Preferably, one or more side ports 116 in communication with infusion lumen 112 are also provided along the distal end of catheter 100. Since catheter 100 tapers to a distal end 104 in the embodiment shown, the diameter of infusion port 114 may be insufficient to allow a desired flow of treated fluid into the vessel. Side ports 116 are often particularly useful with catheters having a tapered distal tip, as they provide extra surface area for infusion of treated blood into the vessel.

A small diameter tubular conduit, such as cannula 120, has open ends 122, 124 and is punched or otherwise inserted through an aperture 121 (FIG. 8) formed in the side wall of catheter tubular member 102. Cannula 120 may be sized and configured similar to cannula 70. Typically, cannula 120 will have a diameter of about 0.025 to 0.035 inch (0.635 to 0.889 mm), and a length of about 0.04 to 0.05 inch (1.016 to 1.27 mm). Once again, those skilled in the art will appreciate that these dimensions are provided as examples only, and can be varied in a particular case. Cannula 120 may be formed of any biocompatible composition commonly utilized in the medical arts, such as a plastic, metal, or metal alloy. Cannula 120 extends through the diameter of infusion lumen 112 and passes through septum 111. In a preferred embodiment, cannula 120 is positioned proximal of cut-out 106, along the length of elongated tubular member 102, although such positioning is not required. When positioned as shown in the figures, blood withdrawn through cannula 120 is directed into withdrawal lumen 110.

Although the embodiments described herein relate to dual lumen catheters, those skilled in the art will appreciate that catheters having more than two lumens may be substituted with only minor modification, as long as the particular design provides two discrete lumens that are separated by a septum as described. In addition, in the embodiments described herein, the withdrawal port is oriented proximal to the infusion port along the length of the catheter. This arrangement is preferred for many extracorporeal treatments, such as hemodialysis, since the treated blood is returned to an area distal to the withdrawal port. This promotes the efficiency of the procedure, since the treated fluid returned to the vessel is not thereafter immediately withdrawn and re-transported to the dialyzer for cleaning. However, this arrangement of the lumens is not required for all possible uses of the catheter, and the withdrawal port may be the more distal port if desired.

In addition to the foregoing, those skilled in the art will appreciate that the specific embodiments described herein need not necessarily have the stepped distal arrangement, as shown in the respective embodiments of FIGS. 1-2 and FIGS. 3-5, nor the tapered distal tip as shown in the embodiment of FIGS. 6-9. These arrangements may often be interchanged with each other, and other analogous port arrangements, with only minor modification. The design for a specific embodiment should, however, provide at least two discrete ports, each in communication with a specific lumen, and wherein two of the lumens are separated by a septum as described.

It is therefore intended that the foregoing detailed description be regarded as illustrative rather than limiting, and that it be understood that it is the following claims, including all equivalents, that are intended to define the spirit and scope of this invention.

What is claimed is:

1. A multi-lumen catheter, comprising:
an elongated tubular member having a plurality of lumens extending therein, said tubular member having a withdrawal port in communication with a first lumen for transporting fluid withdrawn from a body vessel, and an infusion port in communication with a second lumen for return of said fluid to said vessel, said withdrawal port positioned proximal of the infusion port along a length of said tubular member, said tubular member including a septum separating said first and second lumens and extending at least substantially to said infusion port, said tubular member further comprising a passageway formed in an outer wall of said tubular member adjacent said infusion lumen and extending through said septum to said withdraw lumen, and a generally tubular conduit extending through said passageway and septum such that said withdraw lumen communicates with an environment exterior of said tubular member outer wall, said tubular member configured such that at least a portion of said septum extending between said withdrawal port and said infusion port is uncovered, said uncovered portion of said septum including at least one aperture.

2. The multi-lumen catheter of claim 1, further comprising a stepped axial surface along a distal length of said elongated tubular member.

3. The multi-lumen catheter of claim 1, wherein said uncovered septum portion includes a plurality of apertures.

4. The multi-lumen catheter of claim 1, wherein said lumens are generally D-shaped.

5. A multi-lumen catheter, comprising:
an elongated tubular member having a plurality of lumens extending therein, said tubular member having a withdrawal port in communication with a first lumen for transporting fluid withdrawn from a body vessel, and an infusion port in communication with a second lumen for return of said fluid to said vessel, said withdrawal port positioned proximal of said infusion port along a length of said tubular member, said tubular member including a septum separating said first and second lumens, said tubular member further comprising a passageway formed in an outer wall of said tubular member adjacent said infusion lumen and extending through said septum to said withdrawal lumen, and a generally tubular conduit extending through said passageway and septum such that said withdrawal lumen communicates with an environment exterior of said tubular member outer wall.

6. The multi-lumen catheter of claim 5, wherein said conduit comprises a cannula formed of a biocompatible plastic, metal or metal alloy.

7. The multi-lumen catheter of claim 6, wherein said cannula has a diameter of about 0.635 to 0.889 mm.

8. The multi-lumen catheter of claim 6, wherein said cannula has a length of about 1.016 to 1.27 mm.

9. The multi-lumen catheter of claim 5, wherein said catheter comprises a stepped axial surface along a distal length of said elongated tubular member.

10. The multi-lumen catheter of claim 5, wherein at least a portion of said septum extending between said withdrawal port and said infusion port is uncovered, said uncovered portion of said septum including at least one aperture.

11. A multi-lumen catheter for use in extracorporeal treatment of a bodily fluid of a patient, comprising:
an elongated tubular member having a proximal end, a distal end, a pair of lumens extending therein, and a septum separating said lumens in an interior space of said elongated member, a first one of said lumens comprising a withdrawal lumen, and a second one of said lumens comprising an infusion lumen, a withdrawal port disposed along a length of said tubular member in communication with said withdrawal lumen for receiving said bodily fluid from a body vessel for transport to a treatment unit, and an infusion port disposed along a length of said tubular member in communication with said infusion lumen for returning treated bodily fluid to said vessel, said tubular member further comprising a passageway formed in an outer wall of said tubular member generally adjacent said infusion lumen and extending through said septum, and a generally tubular conduit extending along said passageway, through said infusion lumen and said septum into said withdrawal lumen, such that said withdrawal lumen communicates with an environment exterior of said tubular member outer wall, said generally tubular conduit comprising a cannula formed of a biocompatible plastic, metal, or metal alloy.

12. The multi-lumen catheter of claim 11, wherein said distal end of said tubular member tapers to a distal tip, and wherein said infusion port comprises an opening at said distal tip.

13. The multi-lumen catheter of claim 11, further comprising at least one side port disposed along a length of said elongated member in communication with said infusion lumen for returning treated bodily fluid into said vessel.

14. The multi-lumen catheter of claim 11, wherein said passageway and said generally tubular conduit are disposed proximal to said withdrawal port along a length of said elongated tubular member.

15. The multi-lumen catheter of claim 11, wherein said withdrawal port comprises a cut-out portion formed along a length of said elongated member.

16. The multi-lumen catheter of claim 15, wherein said passageway is formed on a side of said elongated member opposite said cut-out portion.

17. The multi-lumen catheter of claim 16, wherein said passageway is proximal of said withdrawal port along a length of said elongated member.

18. The multi-lumen catheter of claim 11, wherein said cannula has a diameter of about 0.635 to 0.889 mm, and a length of about 1.016 to 1.27 mm.

* * * * *